United States Patent [19]

Myers

[11] Patent Number: 6,023,324
[45] Date of Patent: Feb. 8, 2000

[54] PARTICLE FLOW MONITOR AND METERING SYSTEM

[75] Inventor: John L. Myers, Panorama City, Calif.

[73] Assignee: Comco, Inc., Burbank, Calif.

[21] Appl. No.: 08/965,013

[22] Filed: Nov. 5, 1997

[51] Int. Cl.[7] .................................................. G01N 21/00
[52] U.S. Cl. ............................................. 356/73; 356/339
[58] Field of Search ..................................... 356/733, 339, 356/39, 104, 336

[56] References Cited

U.S. PATENT DOCUMENTS

| | | | |
|---|---|---|---|
| 3,781,112 | 12/1973 | Groner et al. | 356/73 |
| 5,047,963 | 9/1991 | Kosaka | 356/339 |

*Primary Examiner*—Frank G. Font
*Assistant Examiner*—Roy M. Punnoose

[57] ABSTRACT

A method and apparatus for determining the flow of abrasive particles in a micro abrasive blasting machine. The machine propels abrasive particles using a carrier stream of compressed gas, typically air, nitrogen or carbon dioxide. The machine mixes the abrasive particles such as aluminum oxide, glass bead, sodium bicarbonate, or silicon carbide, with the carrier gas stream. This mixture is then directed at a work piece through a hard nozzle, typically carbide or sapphire. The apparatus operates on a particle flow detection area upstream of the nozzle through which the carrier stream containing the abrasive particles flows. The apparatus analyzes the fluctuations in the optical transmissivity of the carrier stream containing the abrasive particles to determine the flow of the abrasive particles in the carrier stream.

26 Claims, 6 Drawing Sheets

PARTICLE FLOW MONITOR AND METERING SYSTEM

BACKGROUND OF THE INVENTION

Having a system to monitor and determine a particle flow in devices which use abrasive materials in a process stream, and which minimizes the maintenance and calibration of such a device, while providing process repeatability is highly desirable.

This invention relates to monitoring and determining a particle flow in a process stream. In particular, it is for use with a micro abrasive blasting machine. More particularly, the invention relates to a method and apparatus for opto-electronically determining a flow of abrasive particles in such a machine.

Of the various particle flow monitoring techniques in use in the industry, only a few address the measurement of particle flow in a process stream. The prior optical techniques rely on measurement of the optical density, scatter, or reflectivity of the particles in the process stream. All of these techniques have difficulty, at low particle densities, with contamination of the optical surfaces exposed to the process stream. Where a known zero particle flow condition can be achieved, it is possible to overcome this difficulty by frequent calibration or "zero setting." In many cases, however, calibration is inconvenient or impossible.

One of the prior techniques measures and calibrates the capacitance changes due to the particle content of the stream. However, this technique works better at high stream densities, because maintaining accuracy at very low densities is difficult. Other prior techniques employ acoustic damping or backscatter measurements, but these methods are more suited to large size streams. Yet other of the prior techniques detect and quantify particle impacts on a probe with acoustic or electronic detectors. In small high velocity abrasive streams, however, the probes are subject to rapid damage, which results in frequent maintenance. Accordingly, there is a need to provide a method and apparatus which minimizes these difficulties.

SUMMARY OF THE INVENTION

By this invention there is provided a method and apparatus for monitoring and determining an abrasive particle flow in the process stream of a micro abrasive blasting machine.

According to the invention there is provided a method and apparatus for determining a flow of particles in a process stream comprised of a carrier fluid stream and the particles. There is an optical source which projects a source beam of light through a particle flow detection area along the process stream. Particles moving with the process stream at the particle flow detection area modulate the source beam of light, and the resulting beam of light illuminates an optical receiver. The optical receiver sends a modulated DC output signal to a signal processor. The signal processor processes the DC output signal to yield a processed signal which, in turn, is sent to an output or other device.

In a preferred form of the invention which enables quantitative measurement of the particle flow, the source beam of light is collimated with a collimating lens and passed through a slit aperture in a plate prior to encountering the process stream at the particle flow detection area. The particle flow detection area in a preferred form is thinned and shaped substantially flat-sided, which provides a superior optical path through the process stream and enhances the sensor's quantitative measurement capability. In a preferred form where the process stream is carried in a circular cross-section tube, the process stream at the particle flow detection area is thinned approximately 50% to 70% relative to the diameter of the tube upstream of the particle flow detection area. Upon exiting the process stream, the resultant beam of light is passed through a slit aperture in another plate and refocused with a focusing lens onto the optical receiver.

Also in a preferred form, a sensor control loop returns a feedback control signal to the optical source. The control loop is filtered such that the DC output signal from the optical receiver is slowly maintained at a desired level via the feedback control signal. Further in a preferred form, the processed signal from the signal processor is linear with particle flow volume.

In one aspect of the invention, the carrier fluid may be any suitable fluid or gas in a desired operating environment, so long as it is optically transmissive at a desired operating optical source wavelength. Forms of carrier fluid include water, air, nitrogen, carbon dioxide, and the like in compressed, ambient or partially vacuous states.

In another aspect of the invention, the particles in the process stream include particles selected by an user for a particular application, such as aluminum oxide, glass bead, sodium bicarbonate, silicon carbide, and the like. The particles in the process stream may alternately be provided by an outside environment such as industry generating waste products and the like, or by natural phenomena generating dust and the like.

In yet another aspect of the invention, the particle flow detection area along the process stream in a preferred form is shaped by urging a circular cross-section, flexible tube carrying the process stream into a substantially flat-sided shape between optically transmissive "pinch windows" made of glass, plexiglass, plastic and the like. Alternately, a non-circular cross-section tube carrying the process stream which is suited to acquiring the desired shape at the particle flow detection area, may be used. A thinned or substantially flat-sided particle flow detection area may alternately be formed by any method and with any material as long as it is optically transmissive and the process stream flows through it. For example, the particle flow detection area may be formed itself from a substantially inflexible material such as plexiglass, glass, plastic and the like. Inlet and outlet tubes to the particle flow detection area in this example may be of any suitable shape or form.

Other embodiments of the present invention include smokestack or exhaust gas particulate monitoring, rainfall rate metering, and monitoring filter bag failures in dust collection systems.

The invention is now further described with reference to the accompanying drawings.

DETAILED DESCRIPTION OF THE PREFERRED EMBODIMENT

Referring to FIGS. 1a, 2a, 3a, 4a, 5a, 6 and 7 illustrate an embodiment of the apparatus which quantitatively determines the flow of particles in a process stream. It is referred to as a "preferred embodiment". FIGS. 1b, 2b, 3b, 4b and 5b illustrate an embodiment of the apparatus which monitors whether particles are flowing in a process stream. It is referred to as a "simplified" embodiment.

Figure 1A:
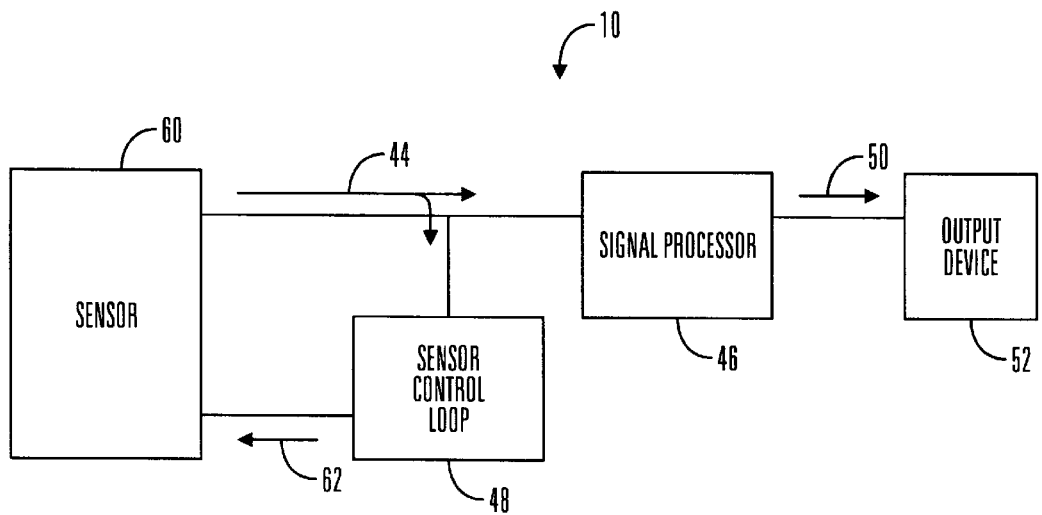
FIG. 1a is a block diagram of a preferred embodiment of the apparatus.
Figure 1B:
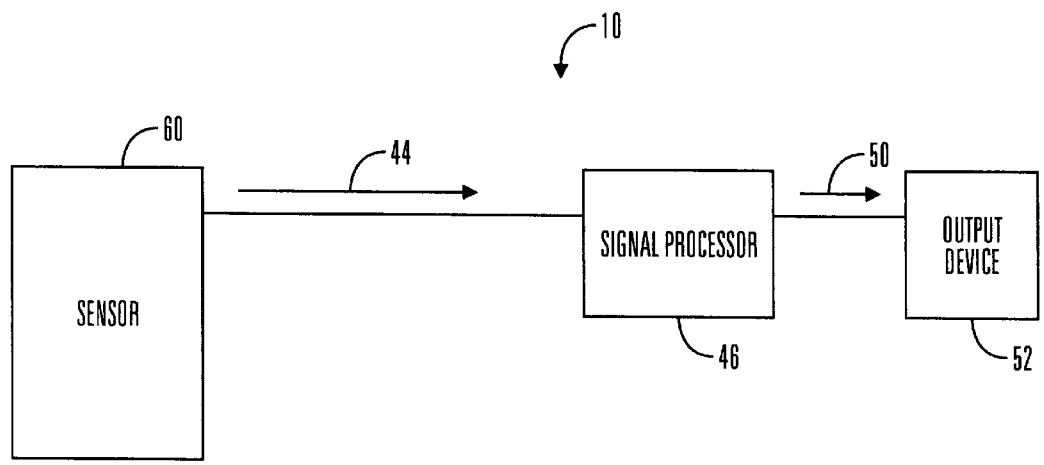
FIG. 1b is a block diagram of a simplified embodiment of the apparatus.

FIGS. 1a and 1b illustrate block diagrams of an apparatus 10 for determining the flow of particles in a process stream. FIG. 1a presents a preferred embodiment. It comprises a sensor 60, an sensor control loop 48, a signal processor 46 and an output or other device 52. The sensor 60 generates and sends a modulated DC output signal designated by arrow 44 to the sensor control loop 48 and the signal processor 46. The sensor control loop returns a feedback control signal designated by arrow 62 to the sensor 60. The signal processor 46 sends a processed output signal designated by arrow 50 to the output or other device 52. FIG. 1b shows a simplified embodiment. It does not contain a sensor control loop 48, and may have a simplified sensor 60 and signal processor 46.

Figure 2A:
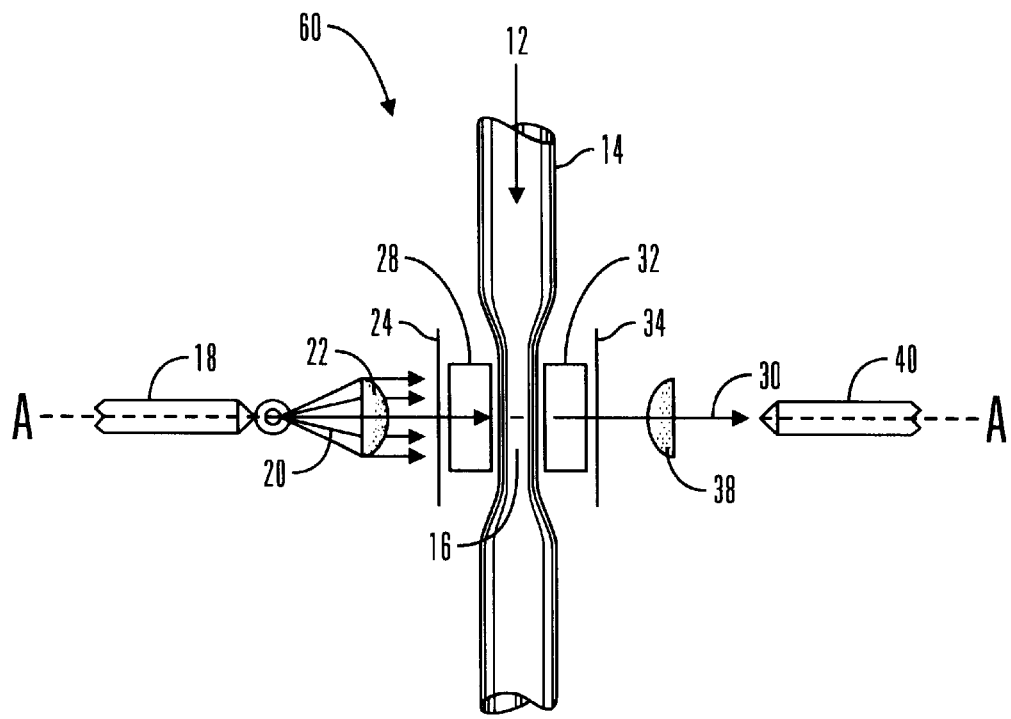
FIG. 2a is a plan view illustrating a preferred embodiment of the sensor at the particle flow detection area.

FIGS. 2a–5b illustrate the sensor 60. FIG. 2a presents a preferred embodiment. At the particle flow detection area 16, the process stream designated by arrow 12 is contained within a tube 14 which is optically transmissive at least at the particle flow detection area 16. An optical source 18 projects a source beam of light designated by arrows 20 through a collimating lens 22, a first plate 24 having a slit aperture 26 and a first pinch window 28 which is optically transmissive, and then through the tube 14 containing the process stream 12 at the substantially flat-sided particle flow detection area 16. The resultant beam of light designated by arrows 30 then passes through a second pinch window 32 which is optically transmissive, a second plate 34 having a slit aperture 36, and a focusing lens 38 which refocuses the resultant beam of light 30 onto an optical receiver 40.

Figure 2B:
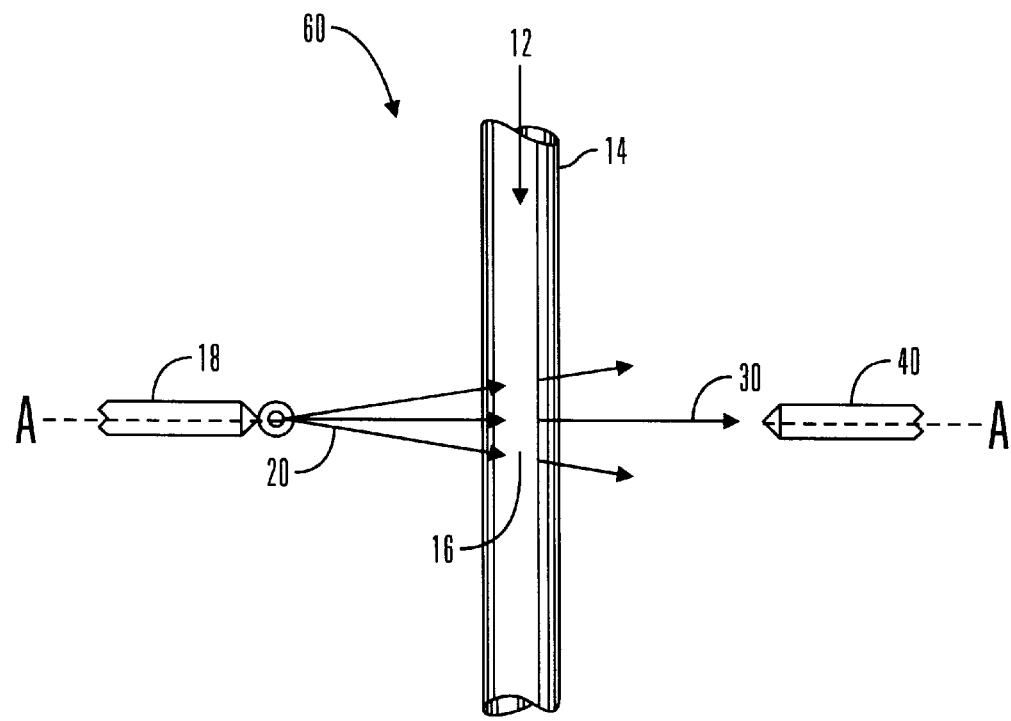
FIG. 2b is a plan view illustrating a simplified embodiment of the sensor at the particle flow detection area.

FIG. 2b depicts a simplified embodiment which does not contain a collimating lens 22, a first plate 24 having a slit aperture 26, a second plate 34 having a slit aperture 36, and a focusing lens 38. As shown, it is not required that the particle flow detection area 16 in this simplified embodiment be substantially flat-sided. The optical source 18 projects a source beam of light designated by arrows 20 through the tube 14 containing the process stream 12 at the particle flow detection area 16. A resultant beam of light designated by arrows 30 then illuminates an optical receiver 40.

Figure 3A:
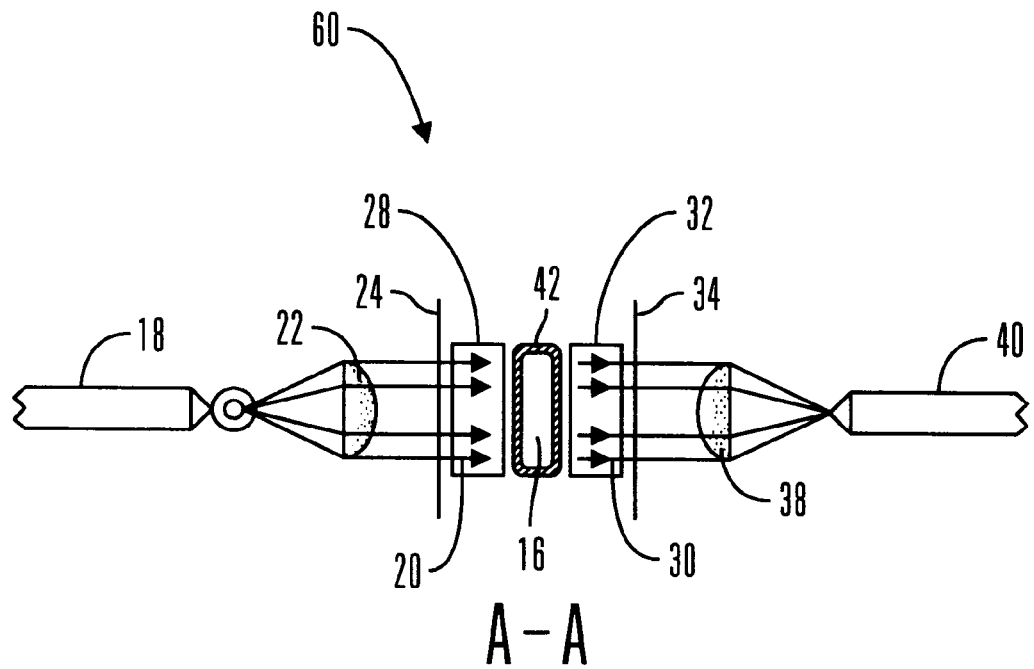
FIG. 3a is a cross-sectional view A—A of a preferred embodiment of the sensor at the particle flow detection area.
Figure 3B:
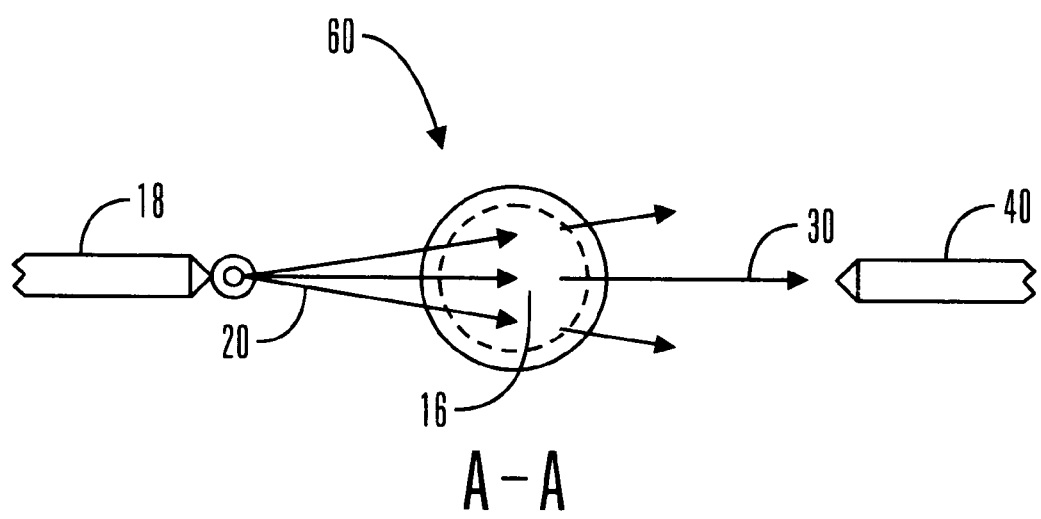
FIG. 3b is a cross-sectional view A—A of a simplified embodiment of the sensor at the particle flow detection area.

FIGS. 3a and 3b illustrate cross-sectional views A—A of the particle flow detection area 16. As shown in FIG. 3a, in a preferred embodiment, the particle flow detection area 16 is created at a desired point along the tube 14 containing the process stream 12 by forming the tube into a substantially flat-sided shape as shown in the cross-section 42 between the first pinch window 28 and the second pinch window 32. In a preferred embodiment where an approximately ¼ inch tube carries the process stream, the process stream is thinned to about 1/16 inch at the particle flow detection area. In another preferred embodiment where an approximately 3/8 inch tube carries the process stream, the process stream is thinned to about 1/10 inch at the particle flow detection area. FIG. 3b presents a particle flow detection area 16 for a simplified embodiment.

Figure 4A:
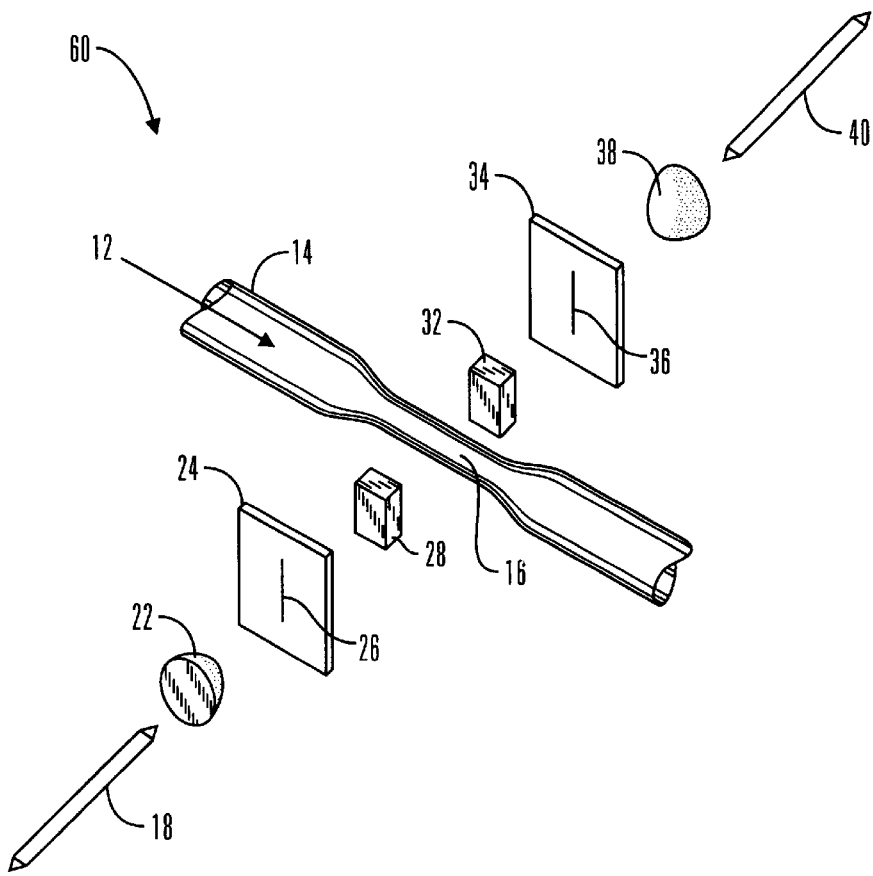
FIG. 4a is an exploded perspective view of a preferred embodiment of the sensor.
Figure 4B:
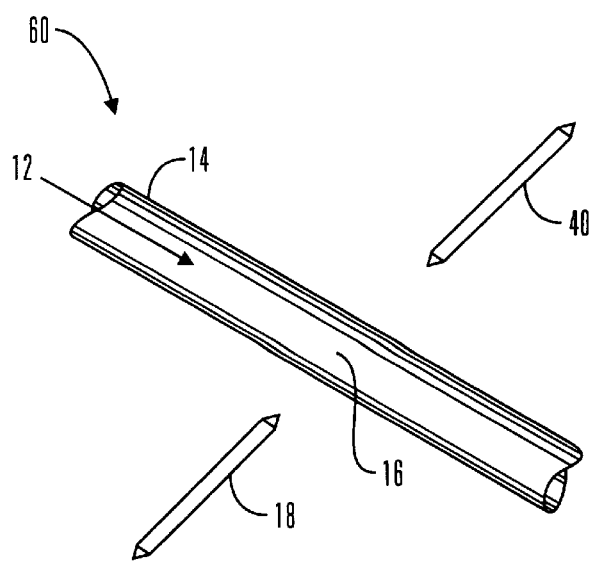
FIG. 4b is an exploded perspective view of a simplified embodiment of the sensor.

FIGS. 4a and 4b depict exploded views of the sensor hardware elements. FIG. 4a shows a preferred embodiment of the sensor 60 showing the sensor hardware element orientations with respect to the tube 14 containing the process stream 12 at the particle flow detection area 16, and to one another. More particularly, it illustrates the positional and alignment relationship between of the first plate 24 and its slit aperture 26, and the second plate 34 and its slit aperture 36. FIG. 4b presents an exploded view of a simplified embodiment of the sensor 60.

Figure 5A:
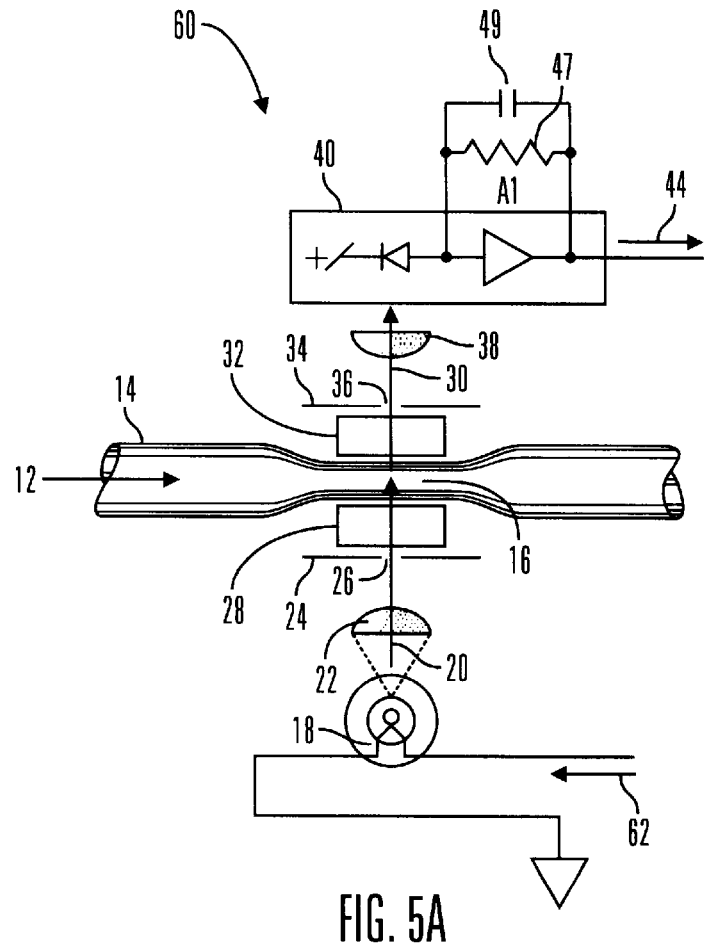
FIG. 5a is a schematic of the sensor for a preferred embodiment of the apparatus.
Figure 5B:
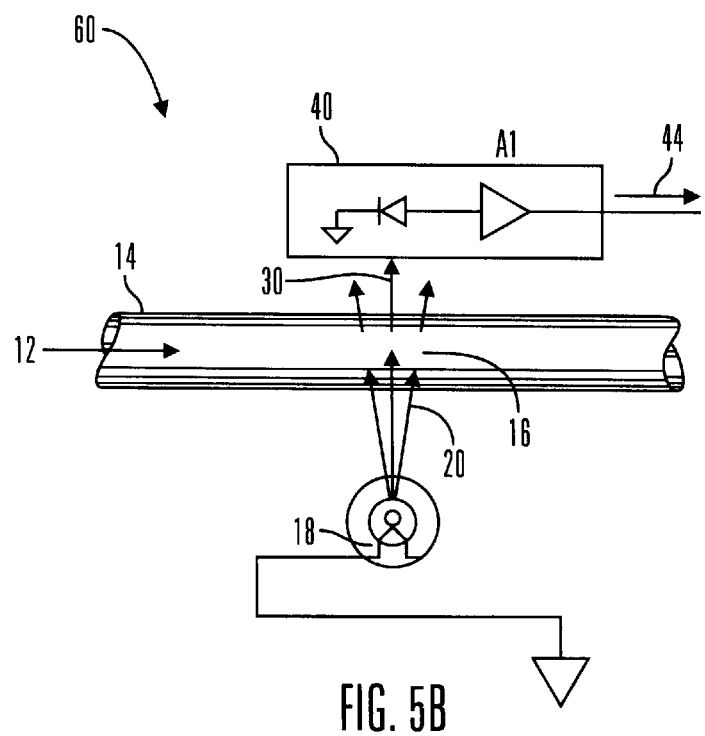
FIG. 5b is a schematic of the sensor for a simplified embodiment of the apparatus.

FIGS. 5a and 5b show schematics of the sensor 60. Referring to FIG. 5a, the optical receiver 40, comprising an integrated detector amplifier integrated circuit (IC), generates and sends a modulated DC output signal designated by arrow 44 to the signal processor 46 and to the sensor control loop 48. A feedback control signal 62 from the sensor control loop 48 is shown as an input to the optical source 18. The transimpedance amplifier gain and passband shape are controlled by resister and capacitor elements 47 and 49, typically 1.0 MEGOHM and 1 microfarad. A broadband logarithmic receiver is preferred if the optical density of the stream becomes greater than a few percent. FIG. 5b depicts a schematic of a simplified embodiment, which does not provide for a feedback control signal 62 to the optical source 18, and uses a photo diode in the photo-voltaic mode to make the output relatively independent of light levels.

Figure 6:
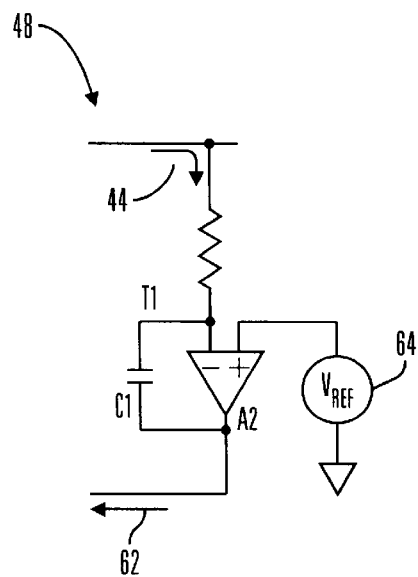
FIG. 6 is a schematic of the sensor control loop for a preferred embodiment of the apparatus.

FIG. 6 illustrates a sensor control loop 48 schematic for a preferred embodiment. The sensor control loop 48, which is filtered to respond only very slowly, sends a feedback control signal 62 to the optical source 18 so that the DC output signal 44 from the optical receiver 40 is maintained at a desired preset level 64. A sensor control loop 48 is not required for a simplified embodiment.

Figure 7:
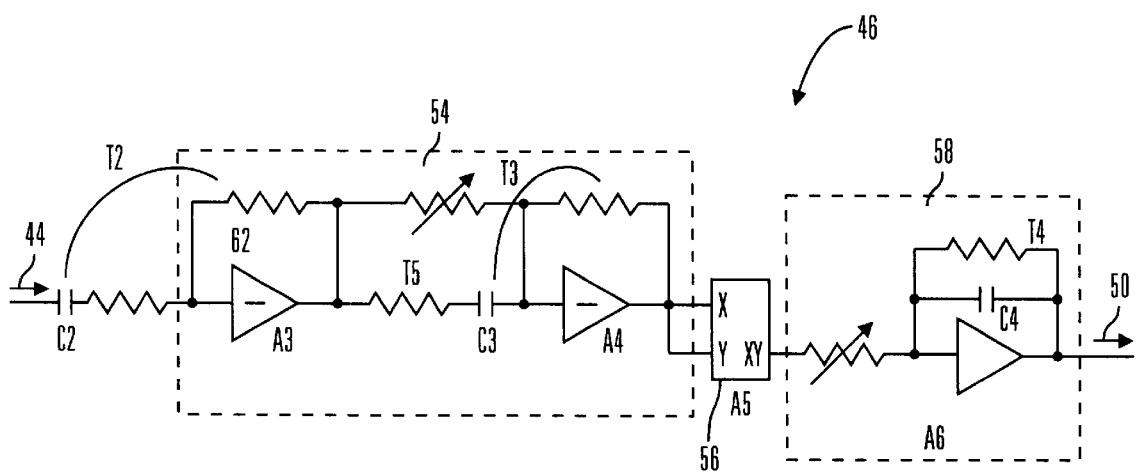
FIG. 7 is a schematic of the signal processor for a preferred embodiment of the apparatus.

FIG. 7 shows a signal processor 46 schematic for a preferred embodiment. The signal processor 46 is first capacitively coupled to the optical receiver 40 to provide a flat response from about 60 Hertz up. The signal is then amplified by a two-stage amplifier 54, which is designed to provide an adjustable transition from flat response to a +6 db/octave slope. In the preferred embodiment, the transition is adjustable from about 1 kHz to about 20 kHz, and the +6 db/octave slope is maintained to about 200 kHz. Above this level, the response is flat for only about an octave before the optical receiver 40, and the alternating current (AC) amplifiers all start to roll off, terminating the passband at about −18 db/octave. The second flat buffer stage provides solid drive and adjustable gain into a high frequency analog multiplier 56. Used in the signal squaring mode, the high frequency analog multiplier 56 squares and rectifies the AC signal from the two stage amplifier 54. The noisy DC signal out of the high frequency analog multiplier 56 is then filtered and amplified 58 to complete the operations of the signal processor 46. Although it is not required, a preferred embodiment signal processor schematic depicted in FIG. 7 may be utilized for a simplified embodiment.

Although the invention has been described in its electronic aspects utilizing some discrete parts and some ICs, it is to be understood that the description given is for several possible embodiments of the invention, and the functions illustrated may be accomplished in other embodiments using any other equivalent devices.

The above specification, examples and data provide a complete description of the manufacture and use of the composition of the invention. Since many example embodiments of the invention can be made without departing from the spirit and scope of the invention, the invention resides in the following claims.

What is claimed is:

1. An apparatus for determining a flow of particles in a process stream, comprising:
   an optical source;
   a particle flow detection area through which a process stream flows, the process stream, which may contain a large number of particles in the detection area at any one time, wherein the optical source is positioned on one side of the particle flow detection area;
   an optical receiver positioned on an opposite side of the particle flow detection area relative to the position of the optical source,
   the optical source, the particle flow detection area, the process stream and the optical receiver being coaligned such that when the optical source projects a beam of light, the beam is transmitted through the particle flow detection area and the process stream and the beam acting to illuminate the optical receiver, such that the optical receiver is responsive effectively to shadows cast by the particles passing through the flow detection area between the optical source and the receiver; and
   a signal processor coupled to the optical receiver, the signal processor being for measuring the high frequency modulation of the optical transmissivity of the process stream thereby to determine the flow of particles in the process stream, and for effecting high pass filtering thereby to render the determination of flow in a defined time period substantially independent of particle velocity in the flow detection area.

2. An apparatus for determining a flow of particles in a process stream, comprising:
   an optical source;
   a particle flow detection area through which a process stream which process stream may contain a large number of particles in the detection area at any one time flows, the particle flow detection area including a first substantially flat-side, and wherein the optical source is positioned proximate to the first substantially flat side;
   an optical receiver positioned on an opposite side of the particle flow detection area relative to the position of the optical source, the optical receiver being proximate to a second substantially flat side of the particle flow detection area,
   the optical source, the particle flow detection area, the process stream and the optical receiver being coaligned such that when the optical source projects a beam of light, the beam is transmitted through the particle flow detection area and the process stream and the beam acting to illuminate the optical receiver, such that the optical receiver is responsive effectively to shadows cast by the particles passing through the flow detection area between the optical source and the receiver; and
   a signal processor coupled to the optical receiver, the signal processor being for measuring the high frequency modulation of the optical transmissivity of the process stream thereby to determine the flow of particles in the process stream, and for effecting high pass filtering thereby to render the determination of flow in a defined time period substantially independent of particle velocity in the flow detection area.

3. An apparatus as claimed in claim 2, further including:
   a collimating lens positioned between the optical source and the particle flow detection area;
   a first plate having a slit aperture positioned between the collimating lens and the particle flow detection area;
   a focusing lens positioned between the optical receiver and the particle flow detection area;
   a second plate having a slit aperture positioned between the focusing lens and the particle flow detection area, the first plate and the second plate being aligned such that each slit aperture is orientated at a right angle to the direction of the process stream,
   the collimating lens, the first plate, the focusing lens and the second plate being linearly coaligned with the optical source, the particle flow detection area, the process stream and the optical receiver such that when the optical source projects a beam of light, the beam is transmitted through the collimating lens, the slit aperture in the first plate, the particle flow detection area, the process stream, the slit aperture in the second plate and the focusing lens, and illuminates the optical receiver;
   a sensor control loop coupled to the optical receiver and the optical source, the sensor control loop being for varying the output of the optical source; and
   an output device coupled to the signal processor, the output device being for indicating the flow of particles in the process stream.

4. An apparatus as claimed in claim 2, wherein the particle flow detection area is formed by locating at least one optically transmissive block against a flexible, optically transmissive tube through which the process stream flows.

5. An apparatus as claimed in claim 2, wherein the particle flow detection area is formed from a substantially rigid optically transmissive material.

6. An apparatus as claimed in claim 1, wherein the optical source is a light emitting diode, or a tungsten filament lamp.

7. An apparatus as claimed in claim 1, wherein the process stream at the particle flow detection area is deformed relative to a shape of the process stream upstream of the particle flow detection area.

8. An apparatus as claimed in claim 2, wherein the optical source is a light emitting diode, or a tungsten filament lamp.

9. An apparatus as claimed in claim 2, wherein the signal processor includes an active precision rectifier.

10. An apparatus as claimed in claim 2, wherein the signal processor includes a high frequency analog multiplier, and wherein the multiplier squares an AC signal received from an amplifier thereby to cause the output signal to be substantially linear relative to the volume or mass of particles per unit of time.

11. An apparatus as claimed in claim 1, wherein the optical receiver is a photodiode, or a photo-diode operated in a photo-voltaic mode.

12. An apparatus as claimed in claim 3, wherein the optical receiver is a linear photo device.

13. An apparatus as claimed in claim 3, wherein the output device is additionally coupled to a particle input control system which varies a particle input into the process stream.

14. An apparatus as claimed in claim 1, further including an output device coupled to the signal processor, the output device being for indicating the flow of particles in the process stream.

15. An apparatus as claimed in claim 14, wherein the signal processor is additionally for determining whether the particle flow in the process stream is relative to at least one preset threshold.

16. An apparatus as claimed in claim 15, wherein the output device is coupled to an alarm.

17. An apparatus as claimed in claim 3, wherein the signal processor is additionally for determining whether the particle flow in the process stream is relative to at least one preset threshold.

18. An apparatus as claimed in claim 17, wherein the output device is coupled to an alarm.

19. A method for determining a flow of particles in a process stream by projecting a beam of light through the process stream and analyzing the fluctuations in optical transmission of the process stream caused by the particles flowing in the process stream to determine the flow of the particles, comprising the steps of:

locating along a process stream a particle flow detection area through which the process stream flows, which process stream may contain a large number of particles in the detection area at any one time;

projecting a source beam of light through the process stream at the particle flow detection area;

receiving a resultant beam of light;

measuring the resultant beam of light to determine the flow of particles in the process stream;

indicating data in response to the measurement caused by the flow of particles in the process stream; and effecting high pass filtering of data thereby to render the determination of flow in a defined time period substantially independent of particle velocity in the flow detection area.

20. A method as claimed in claim 19, further comprising the steps of:

forming the process stream at the particle flow detection area into a substantially flat-sided shape;

varying the source beam of light to maintain the resultant beam of light at a desired level;

collimating the source beam of light and passing the beam through a slit aperture prior to encountering the process stream;

passing the resultant beam of light through a slit aperture and refocusing the beam after exiting the process stream; and measuring the resultant beam of light to quantitatively determine the flow of particles in the process stream.

21. An apparatus as claimed in claim 1, wherein the signal processor includes a high frequency analog multiplier, and wherein the multiplier squares an AC signal received from an amplifier thereby to cause the output signal to be substantially linear relative to the volume or mass of particles per unit time in the process stream.

22. A method as claimed in claim 19, wherein the signal processor includes a high frequency analog multiplier, and wherein the multiplier squares an AC signal received from an amplifier thereby to cause the output signal to be substantially linear relative to the number of particles in the defined volume.

23. A method as claimed in claim 19, wherein the optical receiver responds to non-scattered light.

24. An apparatus as claimed in claim 1, wherein the filtering is effected by a +6 db/octave filter.

25. An apparatus as claimed in claim 2, wherein the filtering is effected by a +6 db/octave filter.

26. A method as claimed in claim 19, wherein the filtering is effected by a +6 db/octave filter.

* * * * *